United States Patent
Zhang et al.

(10) Patent No.: US 10,618,981 B2
(45) Date of Patent: Apr. 14, 2020

(54) METHOD OF PREPARING OXIDIZED STARCH HAEMOSTATIC MATERIAL

(71) Applicants: Hangzhou Singclean Medical Products Co., Ltd, Hangzhou, Zhejiang (CN); Zhejiang University of Science and Technology, Hangzhou, Zhejiang (CN)

(72) Inventors: Zhiguo Zhang, Zhejiang (CN); Wei Huang, Zhejiang (CN); Yange Suo, Zhejiang (CN)

(73) Assignees: Hangzhou Singclean Medical Products Co., Ltd., Hangzhou (CN); Zhejiang University of Science and Technology, Hangzhou (CN)

( * ) Notice: Subject to any disclaimer, the term of this patent is extended or adjusted under 35 U.S.C. 154(b) by 98 days.

(21) Appl. No.: 15/607,561

(22) Filed: May 29, 2017

(65) Prior Publication Data
US 2018/0179301 A1 Jun. 28, 2018

(30) Foreign Application Priority Data
Dec. 27, 2016 (CN) .......................... 2016 1 1223882

(51) Int. Cl.
*C08B 37/00* (2006.01)
*C08B 31/18* (2006.01)
*C08B 30/06* (2006.01)
*A61L 15/28* (2006.01)

(52) U.S. Cl.
CPC .............. *C08B 31/18* (2013.01); *A61L 15/28* (2013.01); *C08B 30/06* (2013.01); *A61L 2400/04* (2013.01)

(58) Field of Classification Search
CPC .......... C08B 31/18; C08B 30/06; A61L 15/28
See application file for complete search history.

(56) References Cited

U.S. PATENT DOCUMENTS

| | | | | |
|---|---|---|---|---|
| 3,516,416 A | * | 6/1970 | Ward | A24B 15/165 131/359 |
| 5,821,360 A | * | 10/1998 | Engelskirchen | C08B 15/04 536/124 |
| 5,959,101 A | * | 9/1999 | Engelskirchen | C08B 15/04 510/245 |

* cited by examiner

*Primary Examiner* — Lakshmi S Channavajjala

(57) ABSTRACT

A method of preparing an oxidized starch haemostatic material, including adding a starch raw material to an external circulation pulsatile reactor; switching on a pump to allow inflow of dry air for drying the raw material; switching on a heat exchanger; vacuumizing the reactor; opening a nitrogen dioxide pipeline and a dry air pipeline; pumping in a mixed gas; controlling temperature at 0-120° C. by the heat exchanger; wherein nitrogen dioxide is contacted with the raw material to trigger a selective oxidation reaction and is continuously recycled; an airflow circulation switch is switched on and off at a pulsating ratio of 1:1-10 to carry out airflow pulsation; stopping inflow of nitrogen dioxide and continuing airflow circulation for 5-30 minutes; after completion of the reaction, adjusting to room temperature; vacuumizing the reactor and treating exhaust gas; allowing nitrogen gas to flow in for rinsing the replaced reactor until completion.

17 Claims, 1 Drawing Sheet

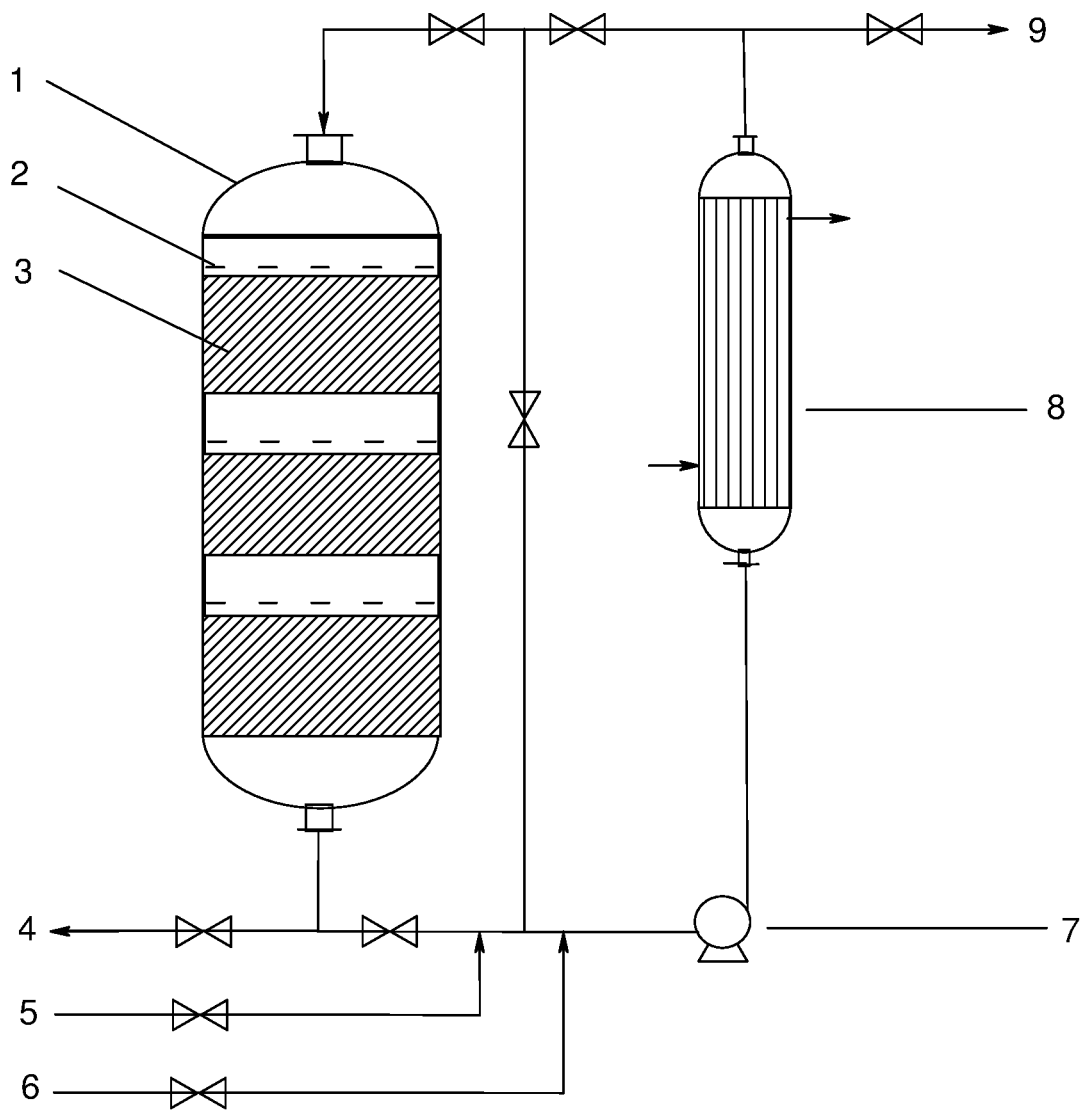

METHOD OF PREPARING OXIDIZED STARCH HAEMOSTATIC MATERIAL

CROSS-REFERENCE TO RELATED APPLICATION

This application claims the benefit of Chinese Patent Application No. 201611223882.3, filed on Dec. 27, 2016, the entire content of which is hereby incorporated by reference.

FIELD OF THE TECHNOLOGY

The present application relates to a method of preparing an oxidized starch haemostatic material.

BACKGROUND

Starch is formed by polymerization of glucose molecules, and is the most common form of storage of carbohydrate in cells. Starch has a general formula of $(C_6H_{10}O_5)_n$. Hydrolysis of starch to a disaccharide stage results in maltose having the chemical formula of $C_{12}H_{22}O_{11}$. Complete hydrolysis of starch results in monosaccharide (glucose), the chemical formula of which being $C_6H_{12}O_6$. There are two types of starch, namely, amylose and amylopectin. Amylose is a non-branched helical structure. Meanwhile, glucose units in amylopectin are linked in a linear manner with α(1→4) glycosidic bonds, while branching takes place with α(1→6) glycosidic bonds occurring every 24 to 30 glucose units.

Oxidized starch is a type of modified starch obtained by reacting starch with an oxidizing agent in an acidic, alkaline or neutral medium so as to oxidize the starch. Oxidized starch lowers the gelatinization temperature, reduces the hot-paste viscosity and increases the thermal stability of starch. The product has a clean white color, transparent paste, good film formation and good resistance to freeze-thaw. As a low-viscosity high-concentration thickener, oxidized starch is widely used in the textile, paper, food and fine chemical industries.

Oxidized starch is one of the modified starches in early uses and researches. Oxidation with hypochlorous acid was already adopted in actual production as early as in the 18th century.

Hydroxyl groups in the starch molecule can be oxidized to carboxyl groups by oxides such as sodium hypochlorite, hydrogen peroxide and ozone.

There are already a wide range of applications of oxidized starch in the industries. Examples of common application of oxidized starch include the paper industry such as coatings or surface sizing, the adhesive industry, the textile industry and the food industry. Traditionally, oxidized starch is prepared by performing oxidation with alkali metal hypochlorite, which is a relatively inexpensive oxidizing agent. Since the oxidizing agent is usually alkali metal hypochlorite, the greater the amount of the oxidizing agent, the greater the risk that the oxidation products at the end of the reaction contain a certain level of chlorine. The reason is apparent in that the presence of chlorine is much undesired in terms of (public) health and the environment.

Cellulose, chitosan and starch are presently the three main classes of polysaccharide haemostatic material. The haemostatic principles of polysaccharide haemostatic materials differ from one type to another. For example, while the haemostatic principles of cellulose and starch both include three types of haemostatic effect, namely, physical, chemical and physiological, there is still difference in the process of physical haemostasis between cellulose and starch. Cellulose exerts physical haemostatic effect mainly by clogging the rupture of capillaries with the material. On the other hand, starch exerts physical haemostatic effect mainly by generating an internal suction due to the swelling of absorbent material, in which the internal suction allows the haemostatic material to adsorb to tangible components, thereby forming a mechanical blood clot. Meanwhile, the chemical and physiological haemostatic principles of cellulose and starch are the same.

Polysaccharide absorbable haemostatic materials are natural macromolecular materials present in a large quantity in nature. Due to various benefits such as a rich source, low prices, good biocompatibility, readily degraded and absorbed in the human body, and low incidence of adverse reactions, polysaccharide has become the focus of current researches in haemostatic material.

SUMMARY

In view of various deficiencies present in the prior art, the present application provides a method of preparing an oxidized starch haemostatic material.

The present application has realized the above objective by means of the following technical solution:

The present application provides a method of preparing an oxidized starch haemostatic material, including:

(1) adding a starch raw material to an external circulation pulsatile reactor; switching on a pump to allow an inflow of dry air for drying the starch raw material; switching on a heat exchanger;

(2) after the starch raw material obtained from step (1) is dried, vacuumizing the external circulation pulsatile reactor;

(3) slowly opening a nitrogen dioxide pipeline; opening a dry air pipeline; pumping in a mixed gas by the pump; controlling a temperature at 0-120° C. by the heat exchanger; wherein nitrogen dioxide is contacted with the starch raw material in the external circulation pulsatile reactor to trigger a selective oxidation reaction, and is continuously recycled to facilitate completion of the selective oxidation reaction; wherein an airflow circulation switch of the external circulation pulsatile reactor is switched on and off at a pulsating ratio of 1:1-10 to carry out an airflow pulsation, which facilitates the selective oxidation reaction;

(4) when the starch raw material obtained from step (3) reaches a targeted level of the selective oxidation reaction, stopping an inflow of the nitrogen dioxide and continuing an airflow circulation for 5-30 minutes; and (5) after completion of the selective oxidation reaction, adjusting the temperature to room temperature; firstly, vacuumizing the external circulation pulsatile reactor and subjecting an exhaust gas to an exhaust gas treatment; then, allowing a nitrogen gas to flow in again to carry out a replacement cycle, and continuing the processes of vacumizing and exhaust gas treatment on the exhaust gas; allowing the nitrogen gas to repeatedly flow in for rinsing the replaced external circulation pulsatile reactor until completion; and obtaining the oxidized starch haemostatic material as an output product.

In a preferred embodiment of the present application, the external circulation pulsatile reactor includes a distributor; wherein the heat exchanger is an external circulation heat exchanger device; wherein an external circulation of airflow is realized by a valve and the pump; wherein the airflow circulation in the external circulation pulsatile reactor is realized by the airflow pulsation in the external circulation pulsatile reactor through opening and closing the valve.

In a preferred embodiment of the present application, the starch raw material is a starch granule, a starch porous material or a starch film material; wherein the starch granule is in a size of 1 to 1,000 micrometer; wherein the starch film material has a thickness of 10 to 1,000 µm.

In a preferred embodiment of the present application, a reaction pressure (gauge pressure) of the external circulation pulsatile reactor is in a range of −0.090 to 1.0 Mpa.

In a preferred embodiment of the present application, a reaction temperature in the external circulation pulsatile reactor is 0-120° C., the nitrogen dioxide in a reaction airflow has a volume concentration of 1-55%.

In a preferred embodiment of the present application, a reaction temperature in the external circulation pulsatile reactor is 0-60° C., the nitrogen dioxide in a reaction airflow has a volume concentration of 2-30%.

In a preferred embodiment of the present application, the airflow circulation switch of the external circulation pulsatile reactor is switched on and off at the pulsating ratio of 1:1-10 to carry out the airflow pulsation, which facilitates the selective oxidation reaction; wherein the airflow pulsation is carried out at a pulsating time of 20-120 seconds: 20-1200 seconds.

In a preferred embodiment of the present application, the oxidized starch haemostatic material has an oxidation degree of 20-100%.

In a preferred embodiment of the present application, the oxidized starch haemostatic material has an oxidation degree of 50-90%.

In a preferred embodiment of the present application, the oxidized starch haemostatic material is used in an absorbable rapid haemostatic material.

The advantageous effects of the present application are as follows:

1. The present application utilizes nitrogen dioxide for the oxidization of the starch. The nitrogen dioxide may selectively oxidize primary hydroxyl groups in the molecular structure of the starch to form carboxyl groups, without producing products such as aldehyde groups. The oxidative selectivity of the nitrogen dioxide is extremely high. Starch is a natural macromolecular compound. The carboxylated starch prepared according to the present application, being a starch derivative, has good biocompatibility, biodegradability and is non-toxic. As a haemostatic material, the carboxyl groups of the oxidized starch cross-link with $Ca^{2+}$ in the plasma, resulting in a reaction between the oxidized starch and the hemoglobin, and the formation of artificial blood clots, thereby exerting a haemostatic effect. Compared with other means of wound bed hemostasis, the present application has the advantages that the oxidized starch may be gradually degraded and does not need to be removed, hence it is more convenient to use.

2. The present application utilizes a mixed gas of nitrogen dioxide and air as the oxidizing agent. By-products such as nitrogen oxides produced during the reaction may be continuously oxidized to form nitrogen dioxide, thereby involving in the oxidation reaction. Through this kind of oxidation cycling process, the usage of reactive raw materials may be reduced, particularly the production of pollutants in the emission may be reduced.

3. The present application utilizes a unique external circulation pulsatile reactor. Based on the test results, the mass transfer rate of the external circulation flow reactor increases by at least an order of magnitude when comparing with the mass transfer rate of the traditional stirred tank reactor. This has greatly facilitated mass transfer between the various reactants in the reactor, thereby making dynamic control of the reaction possible. Moreover, the present application further utilizes an external circulation mode of pulsating airflow. Through the pulsating mode, the flow field in the reactor further realizes sufficient turbulence. Meanwhile, due to the coupling between the pulsating frequency and the reactor, the gas flow field further amplifies the turbulence effect, and eliminates the boundary layer of the surface of the solid raw materials of the reaction, hence further increasing the mass transfer rate of the reaction by at least an order of magnitude. The use of this reaction process is the core and key technology for the present application to realize rapid oxidation reaction.

4. Taking into consideration that it is necessary to timely remove the reaction by-products after the oxidation reaction, the use of the above external circulation pulsatile reactor may also be useful in removing reaction by-products, thereby avoiding partial excessive oxidation and degradation of the products.

5. The concentration of the highly reactive nitrogen dioxide may be adjusted through dilution of the oxidizing agent, so that the oxidation reaction may be controlled more mildly, side effects such as degradation of the products occur less frequently, and the selectivity and yield of the reaction are increased.

6. The present application makes it possible to carry out the reaction under negative pressure and low temperature. This not only further reduces the occurrence of various side effects, but also greatly improves the safety factor of the reaction system.

7. After the reaction is completed, the by-products are timely removed and nitrogen gas after cooling is used for rinsing off the nitrogen-containing materials. As a result, the color of the final products is not affected by the reaction, and yellowing basically does not occur.

8. The present application has the advantage of short reaction time, and may be completed in 1 to 20 hours in general. Meanwhile, the present application also makes it easier to control the degree of oxidation of the products.

9. The present application has strong adaptability, and the oxidized starch as prepared may be used as a high-efficacy absorbable hemostatic material.

BRIEF DESCRIPTION OF THE DRAWING

The FIGURE is a schematic diagram showing the structure of an external circulation pulsatile reactor.

The reference numerals are as follows:
1—Reactor
2—Distributor
3—Starch raw material
4—Exhaust gas treatment
5—Dry air/nitrogen gas
6—Nitrogen dioxide
7—Pump
8—Heat exchanger
9—Exhaust gas treatment

DETAILED DESCRIPTION OF THE EMBODIMENTS

The present application discloses a method of preparing an oxidized starch haemostatic material. The technical solution provided by the present application will now be described in further details with reference to specific embodiments thereof, but the scope of the present application is not limited to the examples.

EXAMPLE 1

1) The starch raw material (granular diameter of 100 to 1,000 micrometer; molecular weight of 30,000 to 2,000,000) was added to the external circulation pulsatile reactor as shown in the FIGURE. The pump was switched on to allow inflow of dry air for drying the starch raw material. The heat exchanger was switched on.

2) After completion of the drying process, the system was vacuumized.

3) The nitrogen dioxide pipeline was slowly opened. The dry air pipeline was opened. The mixed gas was pumped in by the pump. The volume concentration of the nitrogen dioxide was 55%. The airflow temperature was controlled at 0° C. by the heat exchanger. The nitrogen dioxide contacted with the starch raw material in the reactor to trigger selective oxidation reaction, and was continuously recycled to facilitate complete reaction. The pressure in the reactor was −0.090 MPa. The airflow circulation switch of the external circulation oxidation reactor was switched on and off at a pulsating ratio of 20 s:20 s to carry out airflow pulsation, which facilitated the selective oxidation reaction.

4) The inflow of nitrogen dioxide was stopped and the circulation was continued for 30 minutes. The total reaction time was 2 hours.

5) After completion of the reaction, the temperature was adjusted to room temperature. The system was first vacuumized and the exhaust gas was subjected to exhaust gas treatment. Then, nitrogen gas was allowed to flow in again to carry out replacement cycle, and the processes of vacummizing and exhaust gas treatment on the exhaust gas were continued. Nitrogen gas was allowed to repeatedly flow in for rinsing the replacement reactor system until completion. The oxidized starch haemostatic material products were obtained as the output products. The oxidation degree of the obtained oxidized starch products was 20%.

EXAMPLE 2

1) The starch raw material (granular diameter of 1 to 100 micrometer; molecular weight of 20,000 to 200,000) was added to the external circulation pulsatile reactor as shown in the FIGURE. The pump was switched on to allow inflow of dry air for drying the starch raw material. The heat exchanger was switched on.

2) After completion of the drying process, the system was vacuumized.

3) The nitrogen dioxide pipeline was slowly opened. The dry air pipeline was opened. The mixed gas was pumped in by the pump. The volume concentration of the nitrogen dioxide was 1%. The airflow temperature was controlled at 120° C. by the heat exchanger. The nitrogen dioxide contacted with the starch raw material in the reactor to trigger selective oxidation reaction, and was continuously recycled to facilitate complete reaction. The pressure in the reactor was 1.0 MPa. The airflow circulation switch of the external circulation oxidation reactor was switched on and off at a pulsating ratio of 120 s:1200 s to carry out airflow pulsation, which facilitated the selective oxidation reaction.

4) The inflow of nitrogen dioxide was stopped and the circulation was continued for 5 minutes. The total reaction time was 6 hours.

5) After completion of the reaction, the temperature was adjusted to room temperature. The system was first vacuumized and the exhaust gas was subjected to exhaust gas treatment. Then, nitrogen gas was allowed to flow in again to carry out replacement cycle, and the processes of vacummizing and exhaust gas treatment on the exhaust gas were continued. Nitrogen gas was allowed to repeatedly flow in for rinsing the replacement reactor system until completion. The oxidized starch haemostatic material products were obtained as the output products. The oxidation degree of the obtained oxidized starch products was 100%.

EXAMPLE 3

1) The starch raw material (porous starch material; molecular weight of 50,000 to 2,000,000) was added to the external circulation pulsatile reactor as shown in the FIGURE. The pump was switched on to allow inflow of dry air for drying the starch raw material. The heat exchanger was switched on.

2) After completion of the drying process, the system was vacuumized.

3) The nitrogen dioxide pipeline was slowly opened. The dry air pipeline was opened. The mixed gas was pumped in by the pump. The volume concentration of the nitrogen dioxide was 2%. The airflow temperature was controlled at 60° C. by the heat exchanger. The nitrogen dioxide contacted with the starch raw material in the reactor to trigger selective oxidation reaction, and was continuously recycled to facilitate complete reaction. The pressure (gauge pressure) in the reactor was 0.0 MPa. The airflow circulation switch of the external circulation oxidation reactor was switched on and off at a pulsating ratio of 40 s:80 s to carry out airflow pulsation, which facilitated the selective oxidation reaction.

4) The inflow of nitrogen dioxide was stopped and the circulation was continued for 10 minutes. The total reaction time was 2 hours.

5) After completion of the reaction, the temperature was adjusted to room temperature. The system was first vacuumized and the exhaust gas was subjected to exhaust gas treatment. Then, nitrogen gas was allowed to flow in again to carry out replacement cycle, and the processes of vacummizing and exhaust gas treatment on the exhaust gas were continued. Nitrogen gas was allowed to repeatedly flow in for rinsing the replacement reactor system until completion. The oxidized starch haemostatic material products were obtained as the output products. The oxidation degree of the obtained oxidized starch products was 50%.

EXAMPLE 4

1) The starch raw material (starch film; thickness of 10 micrometer) was added to the external circulation pulsatile reactor as shown in the FIGURE. The pump was switched on to allow inflow of dry air for drying the starch raw material. The heat exchanger was switched on.

2) After completion of the drying process, the system was vacuumized.

3) The nitrogen dioxide pipeline was slowly opened. The dry air pipeline was opened. The mixed gas was pumped in by the pump. The volume concentration of the nitrogen dioxide was 30%. The airflow temperature was controlled at 20° C. by the heat exchanger. The nitrogen dioxide contacted with the starch raw material in the reactor to trigger selective oxidation reaction, and was continuously recycled to facilitate complete reaction. The pressure (gauge pressure) in the reactor was −0.040 MPa. The airflow circulation switch of the external circulation oxidation reactor was switched on and off at a pulsating ratio of 20 s:100 s to carry out airflow pulsation, which facilitated the selective oxidation reaction.

4) The inflow of nitrogen dioxide was stopped and the circulation was continued for 10 minutes. The total reaction time was 3 hours.

5) After completion of the reaction, the temperature was adjusted to room temperature. The system was first vacuumized and the exhaust gas was subjected to exhaust gas treatment. Then, nitrogen gas was allowed to flow in again to carry out replacement cycle, and the processes of vacumizing and exhaust gas treatment on the exhaust gas were continued. Nitrogen gas was allowed to repeatedly flow in for rinsing the replacement reactor system until completion. The oxidized starch haemostatic material products were obtained as the output products. The oxidation degree of the obtained oxidized starch products was 90%.

EXAMPLE 5

1) The starch raw material (starch film; thickness of 1,000 micrometer) was added to the external circulation pulsatile reactor as shown in the FIGURE. The pump was switched on to allow inflow of dry air for drying the starch raw material. The heat exchanger was switched on.

2) After completion of the drying process, the system was vacuumized.

3) The nitrogen dioxide pipeline was slowly opened. The dry air pipeline was opened. The mixed gas was pumped in by the pump. The volume concentration of the nitrogen dioxide was 10%. The airflow temperature was controlled at 10° C. by the heat exchanger. The nitrogen dioxide contacted with the starch raw material in the reactor to trigger selective oxidation reaction, and was continuously recycled to facilitate complete reaction. The pressure (gauge pressure) in the reactor was −0.030 MPa. The airflow circulation switch of the external circulation oxidation reactor was switched on and off at a pulsating ratio of 20 s:60 s to carry out airflow pulsation, which facilitated the selective oxidation reaction.

4) The inflow of nitrogen dioxide was stopped and the circulation was continued for 10 minutes. The total reaction time was 4 hours.

5) After completion of the reaction, the temperature was adjusted to room temperature. The system was first vacuumized and the exhaust gas was subjected to exhaust gas treatment. Then, nitrogen gas was allowed to flow in again to carry out replacement cycle, and the processes of vacumizing and exhaust gas treatment on the exhaust gas were continued. Nitrogen gas was allowed to repeatedly flow in for rinsing the replacement reactor system until completion. The oxidized starch haemostatic material products were obtained as the output products. The oxidation degree of the obtained oxidized starch products was 70%.

EXAMPLE 6

1) The starch raw material (starch microsphere; sphere diameter of 50 to 500 micrometer) was added to the external circulation pulsatile reactor as shown in the FIGURE. The pump was switched on to allow inflow of dry air for drying the starch raw material. The heat exchanger was switched on.

2) After completion of the drying process, the system was vacuumized.

3) The nitrogen dioxide pipeline was slowly opened. The dry air pipeline was opened. The mixed gas was pumped in by the pump. The volume concentration of the nitrogen dioxide was 5%. The airflow temperature was controlled at 20° C. by the heat exchanger. The nitrogen dioxide contacted with the starch raw material in the reactor to trigger selective oxidation reaction, and was continuously recycled to facilitate complete reaction. The pressure (gauge pressure) in the reactor was −0.030 MPa. The airflow circulation switch of the external circulation oxidation reactor was switched on and off at a pulsating ratio of 20 s:80 s to carry out airflow pulsation, which facilitated the selective oxidation reaction.

4) The inflow of nitrogen dioxide was stopped and the circulation was continued for 5 minutes. The total reaction time was 2 hours.

5) After completion of the reaction, the temperature was adjusted to room temperature. The system was first vacuumized and the exhaust gas was subjected to exhaust gas treatment. Then, nitrogen gas was allowed to flow in again to carry out replacement cycle, and the processes of vacumizing and exhaust gas treatment on the exhaust gas were continued. Nitrogen gas was allowed to repeatedly flow in for rinsing the replacement reactor system until completion. The oxidized starch haemostatic material products were obtained as the output products. The oxidation degree of the obtained oxidized starch products was 80%.

EXAMPLE 7

Haemostatic Effect of the Oxidized Starch

Test Method:

A swine liver was cut by a scalpel on the surface to remove a liver serous area of 1.5 cm×2.5 cm, creating a bleeding wound with a depth of 0.25 cm. The oxidized starch materials obtained from the above Examples 1 to 6 were used as haemostatic materials for the haemostasis of the above wound, respectively Immediately after bleeding, the oxidized starch haemostatic material was placed on the wound, and medical surgical gloves or haemostatic gauze were used to apply pressure on the oxidized starch haemostatic material to block blood flow. The medical surgical gloves or haemostatic gauze were gently released after 1 to 2 minutes, and the following observations were made: the haemostatic effect; whether starch and blood clot were adhered to the medical surgical gloves or haemostatic gauze; and whether bleeding would occur again upon releasing the medical surgical gloves or haemostatic gauze.

Test Results:

The oxidized starch prepared by Examples 1 to 6 of the present application had good haemostatic effect and was easy to use. All the oxidized starch absorbed blood immediately and formed a viscous starch-clot colloid upon contacting the blood. Effective control of the wound bleeding could all be achieved within 1 minute. There was no adhesion between the clot and the gauze dressings for applying the pressure, and the release of the gauze dressings did not cause bleeding again.

Lastly, it is to be noted that the above are only specific embodiments of the present application. Apparently, the present application is not limited to the above embodiments, and many variations may be made. It will be understood by one skilled in the art that all variations that are directly derived from or contemplate from the disclosure of the present application are considered to be within the scope of the present application.

What is claimed is:

1. A method of preparing an oxidized starch haemostatic material, comprising:
   (1) adding a starch raw material to an external circulation pulsatile reactor; switching on a pump to allow an inflow of dry air for drying the starch raw material; switching on a heat exchanger;
   (2) after the starch raw material obtained from step (1) is dried, vacuumizing the external circulation pulsatile reactor;
   (3) slowly opening a nitrogen dioxide pipeline; opening a dry air pipeline; pumping in a mixed gas by the pump; controlling a temperature at 0-120°C. by the heat exchanger; wherein nitrogen dioxide is contacted with the starch raw material in the external circulation pulsatile reactor to trigger a selective oxidation reaction, and is continuously recycled to facilitate completion of the selective oxidation reaction; wherein an airflow circulation switch of the external circulation pulsatile reactor is switched on and off at a pulsating ratio of 1:1-10 to carry out an airflow pulsation, which facilitates the selective oxidation reaction; wherein an external circulation of airflow is realized by a valve and the pump; wherein the airflow circulation in the external circulation pulsatile reactor is realized by the airflow pulsation in the external circulation pulsatile reactor through opening and closing the valve;
   (4) when the starch raw material obtained from step (3) reaches a targeted level of the selective oxidation reaction, stopping an inflow of the nitrogen dioxide and continuing an airflow circulation for 5-30 minutes; and
   (5) after completion of the selective oxidation reaction, adjusting the temperature to room temperature; firstly, vacuumizing the external circulation pulsatile reactor and subjecting an exhaust gas to an exhaust gas treatment; then, allowing a nitrogen gas to flow in again to carry out a replacement cycle, and continuing the processes of vacummizing and exhaust gas treatment on the exhaust gas; allowing the nitrogen gas to repeatedly flow in for rinsing the replaced external circulation pulsatile reactor until completion; and obtaining the oxidized starch haemostatic material as an output product.

2. The method of claim 1, wherein the external circulation pulsatile reactor comprises a distributor; wherein the heat exchanger is an external circulation heat exchanger device.

3. The method of claim 1, wherein the starch raw material is a starch granule, a starch porous material or a starch film material; wherein the starch granule is in a size of 1 to 1,000 micrometer; wherein the starch film material has a thickness of 10 to 1,000 μm.

4. The method of claim 2, wherein the starch raw material is a starch granule, a starch porous material or a starch film material; wherein the starch granule is in a size of 1 to 1,000 micrometer; wherein the starch film material has a thickness of 10 to 1,000 μm.

5. The method of claim 1, wherein a reaction pressure (gauge pressure) of the external circulation pulsatile reactor is in a range of −0.090 to 1.0 Mpa.

6. The method of claim 5, wherein a reaction temperature in the external circulation pulsatile reactor is 0-120°C., the nitrogen dioxide in a reaction airflow has a volume concentration of 1-55%.

7. The method of claim 1, wherein a reaction temperature in the external circulation pulsatile reactor is 0-60°C., the nitrogen dioxide in a reaction airflow has a volume concentration of 2-30%.

8. The method of claim 2, wherein a reaction temperature in the external circulation pulsatile reactor is 0-60°C., the nitrogen dioxide in a reaction airflow has a volume concentration of 2-30%.

9. The method of claim 5, wherein a reaction temperature in the external circulation pulsatile reactor is 0-60°C., the nitrogen dioxide in a reaction airflow has a volume concentration of 2-30%.

10. The method of claim 6, wherein a reaction temperature in the external circulation pulsatile reactor is 0-60°C., the nitrogen dioxide in a reaction airflow has a volume concentration of 2-30%.

11. The method of claim 1, wherein the airflow circulation switch of the external circulation pulsatile reactor is switched on and off at the pulsating ratio of 1:1-10 to carry out the airflow pulsation, which facilitates the selective oxidation reaction; wherein the airflow pulsation is carried out at a pulsating time of 20-120 seconds:20-1200 seconds.

12. The method of claim 1, wherein the oxidized starch haemostatic material has an oxidation degree of 20-100%.

13. The method of claim 12, wherein the oxidized starch haemostatic material has an oxidation degree of 50-90%.

14. The method of claim 11, wherein the oxidized starch haemostatic material is used in an absorbable rapid haemostatic material.

15. The method of claim 12, wherein the oxidized starch haemostatic material is used in an absorbable rapid haemostatic material.

16. The method of claim 13, wherein the oxidized starch haemostatic material is used in an absorbable rapid haemostatic material.

17. The method of claim 1, wherein a reaction pressure (gauge pressure) of the external circulation pulsatile reactor is under negative pressure range of −0.090 to -0.0 Mpa.

* * * * *